(12) United States Patent
Hu et al.

(10) Patent No.: US 7,508,908 B2
(45) Date of Patent: *Mar. 24, 2009

(54) CT METHOD AND APPARATUS FOR LIQUID SAFETY-DETECTION WITH A RADIATION SOURCE

(75) Inventors: Haifeng Hu, Beijing (CN); Yuanjing Li, Beijing (CN); Kejun Kang, Beijing (CN); Zhiqiang Chen, Beijing (CN); Yinong Liu, Beijing (CN); Yulan Li, Beijing (CN); Li Zhang, Beijing (CN); Wanlong Wu, Beijing (CN); Ziran Zhao, Beijing (CN); Xilei Luo, Beijing (CN); Bin Sang, Beijing (CN)

(73) Assignees: Tsinghua University, Beijing (CN); Nuntech Company Limited, Beijing (CN)

( * ) Notice: Subject to any disclaimer, the term of this patent is extended or adjusted under 35 U.S.C. 154(b) by 201 days.

This patent is subject to a terminal disclaimer.

(21) Appl. No.: 11/286,559

(22) Filed: Nov. 23, 2005

(65) Prior Publication Data
US 2006/0239402 A1      Oct. 26, 2006

(30) Foreign Application Priority Data
Nov. 26, 2004   (CN) ................ 2004 1 0009897
Sep. 22, 2005   (CN) ................ 2005 1 0086458

(51) Int. Cl.
*G01N 23/06*        (2006.01)
(52) U.S. Cl. ......................... 378/54; 378/57
(58) Field of Classification Search ............ 378/53, 378/54, 57, 58, 64, 68, 69
See application file for complete search history.

(56) References Cited

U.S. PATENT DOCUMENTS

| 4,649,483 | A | 3/1987 | Dixon, Jr. ............ 702/12 |
| 5,023,895 | A | 6/1991 | McCroskey et al. ...... 378/4 |
| 5,039,856 | A | 8/1991 | Tron ................ 250/358.1 |
| 5,367,552 | A | 11/1994 | Peschmann .......... 378/57 |
| 6,078,642 | A | 6/2000 | Simanovsky et al. ..... 378/57 |
| 6,151,379 | A | 11/2000 | Kullenberg et al. ...... 378/54 |

(Continued)

FOREIGN PATENT DOCUMENTS

CN          1305610         7/2001

(Continued)

*Primary Examiner*—Courtney Thomas
(74) *Attorney, Agent, or Firm*—Ladas & Parry LLP (57) ABSTRACT

A CT method and an apparatus for liquid safety-detection with a radiation source relate to a radiation imaging detecting technology field. The invention comprises using a radiation source, a detector and data collector, a computer data processor; and the main steps are: 1) a liquid article to be detected being placed onto a rotary platform which is rotatable; 2) the ray emitted from the radiation source passing through the liquid article, and being received and formed into projection data by the detector and data collector; and 3) the projection data being transmitted to the computer data processor, which processes it to obtain the liquid density of the detected article, compares the result with the densities of dangerous articles in a current database, and then visually displays the detected information of the detected liquid article. Comparing to the prior art, the invention has a small volume, a strong anti-interference, a high accuracy of detection, an easy shielding, and a high use safety and reliability.

16 Claims, 6 Drawing Sheets

U.S. PATENT DOCUMENTS

| | | | |
|---|---|---|---|
| 6,418,189 B1 | 7/2002 | Schafer | 378/57 |
| 6,748,043 B1 | 6/2004 | Dobbs | 378/4 |
| 7,386,093 B2 * | 6/2008 | Wu et al. | 378/57 |
| 2004/0081274 A1 | 4/2004 | Kresse et al. | 378/57 |

FOREIGN PATENT DOCUMENTS

| | | |
|---|---|---|
| CN | 1460849 | 12/2003 |
| GB | 2 122 837 | 1/1984 |
| JP | 60-64235 | 4/1985 |
| JP | 9-196865 | 7/1997 |
| JP | 2005-31043 | 2/2005 |
| WO | WO 92/14142 | 8/1992 |
| WO | WO 94/02839 | 2/1994 |
| WO | WO 2004/090576 | 10/2004 |

* cited by examiner

CT METHOD AND APPARATUS FOR LIQUID SAFETY-DETECTION WITH A RADIATION SOURCE

CROSS REFERENCE TO THE RELATED APPLICATIONS

The present application claims the benefits of the Chinese Application No. 200410009897.0 filed with the Chinese Patent Office on Nov. 26, 2004 and the Chinese Application No. 200510086458.4 filed with the Chinese Patent Office on Sep. 22, 2005. The entireties of these two applications are incorporated into this application by reference.

FIELD OF THE INVENTION

The invention relates to a radiation imaging technology field, and in particular, to a CT method and a CT apparatus for liquid safety-detection with a radiation source.

DESCRIPTION OF THE PRIOR ART

In a safety detection system of civil aviation, it is required that the liquid articles taken with passengers are examined without opening them. The detection methods used in the prior art mainly comprise a chemical method, an electromagnetic method and a neutron detection method. The chemical method is again classified into an odor identification method and an ion scanning explosive detection method and the like, which methods in practical applications are frequently subjected to severe affection of sealed and packaged conditions of articles to be detected, and also the chemical method suffers from strong sensitivity and high error detection ratio. The electromagnetic detection method is prone to be electromagnetically interfered due to its weak signal, and can not be used to detect liquid articles with metal packages. The use of the neutron detection method will cause residual radiation to be remained in the detected liquid because of the "neutron activation", and the radiation shielding is complicate and has poor stability, great cover area and high investment, so that the method is not suitable for large scale applications in the safety detection system of civil aviation. In the existing X-ray scanning detection systems, the X-ray passed through a detected article is transmitted to a detector to reflect the density distribution in the detected article depending on the intensity variation of the X-ray, and the intensity of the X-ray is converted into an image grey scale so that the perspective image of the detected article is obtained. Such X-ray scanning detection method, which forms image by identifying the density difference of the detected article, fails to accomplish image formation detection for a liquid article with uniform density distribution.

SUMMARY OF THE INVENTION

In order to overcome the defects existing in the prior art, the purpose of the invention is to provide a CT method and a CT apparatus for liquid safety-detection with a radiation source. It uses a radiation source to detect a packaged liquid article in CT method, so that the density information of the detected liquid is obtained.

In order to achieve the above described purpose, the technical solution of the invention is accomplished in following manner:

A first aspect of the invention is to provide a CT method for liquid safety-detection with a radiation source, which method comprises using a radiation source, a detector and a data collector, and a computer data processor; and the method comprises the main steps of:

1) placing a liquid article to be detected onto a rotary platform which is rotatable;

2) emitting a ray from the radiation source, passing the ray through the liquid article, and receiving the ray and forming it into projection data by the detector and data collector; and 3) transmitting the projection data to the computer data processor; processing it to obtain a liquid density of the detected liquid article; comparing the liquid density of the liquid article with densities of dangerous articles in a current database, and then visually displaying information of the detected liquid article.

The apparatus of the invention has advantages of small volume, high accuracy, strong anti-interference, high safety and reliability, and easy protection, and is applicable to safety detection systems of civil aviation and other important sites.

A second aspect of the invention is a CT apparatus realizing the above described method for liquid safety-detection with a radiation source, which apparatus comprises a radiation source, a detector and data collector, and a computer data processor. Said detector and data collector has integral modular structure, and in the data collector a data amplifying and shaping circuit is included. In the computer data processor a database of substance densities of dangerous articles is included. The features of the apparatus are that said radiation source is located on one side of a rotary platform mechanism on which a liquid article to be detected can be placed, and that said detector and data collector is located on other side of the rotary platform mechanism and faces X, γ ray beams emitted from the radiation source. Data output cables for the detector and data collector are connected with the computer data processor.

In the above described apparatus, said radiation source employs an X-ray machine or an isotope.

In the above described apparatus, said detector employs a solid detector or a gas detector.

In the above described apparatus, said data collector can operates in an electric current integrating manner or in a counting manner.

In the above described apparatus, the coordinate operations of said radiation source, the detector and collector, the computer data processor and the rotary platform mechanism are controlled synchronously by a provided scanning controller.

Since the invention employs the above described method and structure, uses a radiation source to detect a liquid article whose rotation can be controlled, so as to form the density information of the detected liquid article, and then compares density information of the detected liquid article with the density values of dangerous articles in a current database, it is judged whether the detected liquid is a dangerous article or not. Comparing to the prior art, the invention has a small volume, a strong anti-interference, a high detection accuracy, an easy shielding, and a high use safety and reliability.

A third aspect of the invention is a CT apparatus for liquid safety-detection with a radiation source, which apparatus comprises a radiation source, a detector and data collector, and a computer data processor, said detector and data collector having integral modular structure, and in the data collector a data amplifying and shaping circuit being included, in the computer data processor a database of substance densities of dangerous articles being included, characterized by that said radiation source is located on one side of a rotary platform mechanism on which a liquid article to be detected can be placed, that said detector and data collector is located on other side of the rotary platform mechanism and faces the X, γ ray beams emitted from the radiation source, and that the data output cable of the detector and data collector is connected with the computer data processor. Said radiation source employs an X-ray machine or an isotope source. Said detector employs a solid detector or a gas detector. Said data collector can operates in an electric current integrating manner or in a counting manner. The coordinate operations of said radiation source, the detector and collector, the computer data processor and the rotary platform mechanism are controlled synchronously by a provided scanning controller.

A fourth aspect of the invention is a CT method for liquid safety-detection with a radiation source by using the apparatus according to the invention, which method comprises using a radiation source, a detector and a data collector, and a computer data processor; and the method comprises the main steps of:

1) placing a liquid article to be detected onto a rotary platform which is rotatable;

2) emitting a ray from the radiation source, passing the ray through the liquid article, and receiving the ray and forming it into projection data by the detector and data collector; and 3) transmitting the projection data to the computer data processor; processing it to obtain a liquid density of the detected liquid article; comparing the liquid density of the liquid article with the densities of dangerous articles in a current database, and then visually displaying information of the detected liquid article.

A technical solution of a fifth aspect of the invention is as follows:

An apparatus for carrying out CT safety-examination of a liquid article by means of a radiation source, comprises a frame, a radiation source, a detector, a beam guiding box, a data collecting and image processing computer, a system control box, a radiation source controller, and a rotary disk lifting device on which a liquid article to be examined can be placed. The structure features of the apparatus are that said rotary disk lifting device is located in a shield cartridge. The shield cartridge is fixed on one side in the frame, and at the upper opening end of the shield cartridge and at the upper portion of the frame there is provided with a protection shield door which can close the shield cartridge. The outer wall of the shield cartridge is provided with the beam guiding box, the front and rear ends of which are respectively connected with a front collimator device and a rear collimator. The front collimator device is fixedly connected with the radiation source, and the corresponding position of the rear collimator is provided with a device for adjusting horizontally the detector. The detector is mounted to the device for adjusting horizontally the detector. On the other side in the frame and at the bottom of the radiation source there is mounted the radiation source controller. To the upper portion of the radiation source there are successively mounted the data collecting and image processing computer and the system control box. To the top of the frame there may be mounted a touch screen which can display the examination result.

In accordance with the above described technical solution, said rotary disk lifting device comprises a linear slide rail, a lead screw, a slider carrier, a first electric motor, and a rotary disk carrier and a rotary disk which have a second electric motor. The linear slide rail is fixed to the inner wall of the shield cartridge and embedded movably in the slider carrier. The slider carrier is provided inside with an internal thread and thread-connected with the lead screw which is fixed to the upper and lower ends inside the shield cartridge, and the bottom end of the lead screw is connected with the first electric motor. The external edge of the slider carrier is connected with the rotary disk carrier fixed with the second electric motor, and on the rotary disk carrier there is provided with a rotary disk which is connected with the output end of the second electric motor.

In accordance with the above described technical solution, said protection shield door comprises a door plate, two side slide rails, a gear rack, a gear, and an electric motor. The two side slide rails are fixed to the upper plane of the frame and slidably connected with the door plate by bearings, and the gear rack fixed at the bottom of the door plate engages with the gear, which is connected with the electric motor shaft fixed to the lower plane of the frame.

In accordance with the above described technical solution, the shape of the cross section of said beam guiding box is a sector, and the inner wall of the beam guiding box is provided with a protection shield layer.

In accordance with the above described technical solution, said front collimator device comprises an up and down sliding stoppers, a left and right sliding stoppers, and a housing connected with the beam guiding box. The up and down sliding stoppers is embedded in a longitudinal slide slot of the housing and is adjusted by a indexing head first push rod which is connected with the up and down sliding stoppers and slidably fitted to the upper and lower wall surfaces of the housing, to longitudinally move. The left and right sliding stoppers is embedded in a lateral slide slot of the housing and is adjusted by a indexing head second push rod which is connected with the left and ride sliding stopper and slidably fitted to the two side wall surfaces of the housing, to laterally move.

In accordance with the above described technical solution, said rear collimator is constituted by an arc form plate cut with a slit or an arc form plate with grates.

In accordance with the above described technical solution, said detector adjusting device comprises a dovetail slot holder and a slide frame which can embedded in the dovetail slot of the dovetail slot holder. The dovetail slot holder is fixed on a support plate which is connected with the rear collimator and the frame. The detector is mounted on the slide frame and faces a beam exit of the rear collimator. The lateral displacement of the slide frame is adjusted by a indexing head third push rod which is fixed to the frame. On the dovetail slot holder there is provided with screws by which the slide frame can be fixed.

In accordance with the above described technical solution, the periphery of said detector adjusting device is provided with a detector protection case.

In accordance with the above described technical solution, said radiation source consists of an X-ray machine or an isotope source; and the detector consists of a solid or gas detector.

In accordance with the above described technical solution, to the top of the frame there may be mounted a touch screen which can display the examination result.

Since the invention employs the above described structure, uses a radiation source to detect a liquid article the rotation and lift of which can be controlled, so as to obtain the multi-slice density information of the detected liquid article, and then compares density information of the detected liquid article with the density values of dangerous liquids stored in a current database, it is judged whether the detected liquid is a dangerous article or not. Comparing to the prior art, the invention has a small volume, a strong anti-interference, a high detection accuracy, an easy shielding, and a high use safety and reliability.

The invention is further illustrated hereinafter in conjunction with the accompanying drawings and the preferred embodiments.

DETAILED DESCRIPTION OF THE PREFERRED EMBODIMENT

Embodiment 1

Figure 1:
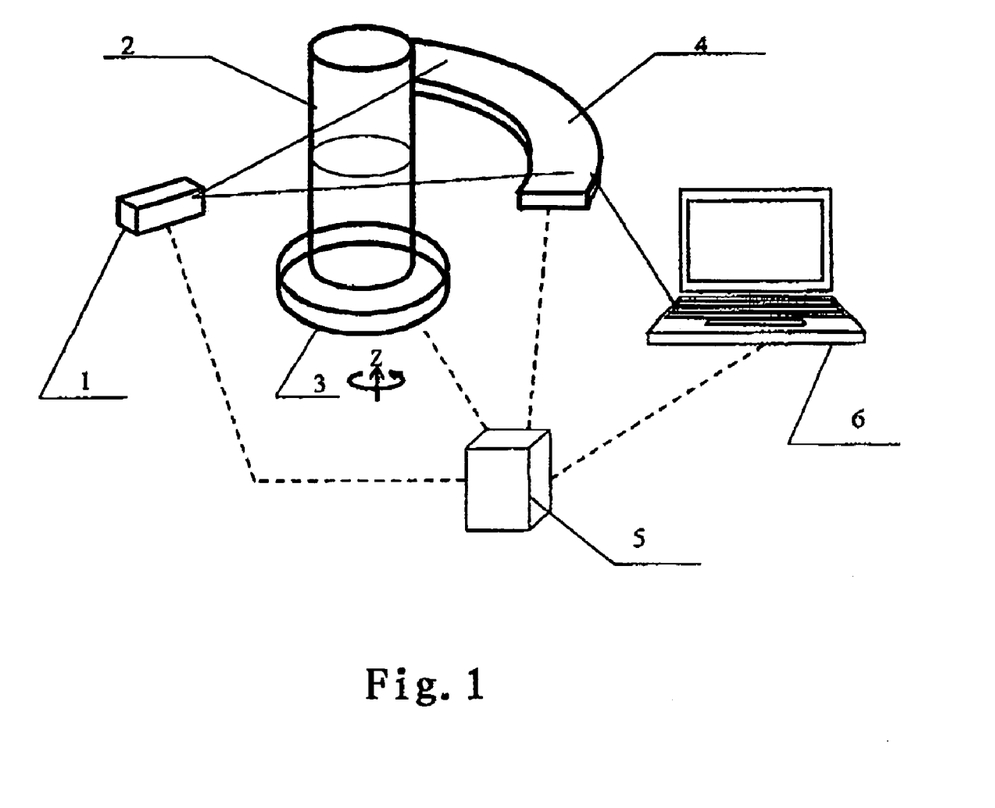
FIG. 1 is a schematic diagram of the structure of Embodiment 1 of the invention.

Referring to FIG. 1, the invention comprises a radiation source 1 employing an X-ray machine or an isotope, a detector and data collector 4 which has an integral modular structure, a computer data processor 6. The detector employs a solid detector or a gas detector, and in the data collector included is a data amplifying and shaping circuit which operates in an electric current integrating manner or in a counting manner. In the computer data processor 6 included is a database of substance densities of dangerous articles. The radiation source 1 is located on one side of a rotary platform 3 on which a liquid article to be detected is placed, and the detector and data collector 4 is located on other side of the rotary platform 3 and face the X, γ ray beams emitted from the radiation source 1. The data output cable of the detector and data collector 4 is connected with the computer data processor 6. The coordinate operations of the radiation source 1, the detector and collector 4, the computer data processor 6 and the rotary platform mechanism 3 are controlled synchronously by a provided scanning controller 5.

The main steps in the application of the apparatus of the invention are:

1) Turn on the power supplies of the radiation source 1, the detector and data collector 4, the computer data processor 6 and the rotary platform mechanism 3, and place a liquid article to be detected onto the rotary platform mechanism 3 which is rotatable.

2) The ray emitted from the radiation source 1 passes through the liquid article, and is received and formed into projection data by the detector and data collector 4 which faces the ray beam. The scanning controller 5 controls the rotary platform mechanism 3 to rotate the liquid article at a certain speed and at same time the detector and data collector 4 collect data at a certain speed under the control of the scanning controller 5, so as to obtain a lot of projection data of such cross section of the liquid article.

3) The projection data is transmitted to the computer data processor 6, which corrects and reconstructs it to calculate the liquid density of the detected article, compares the result with the densities of dangerous articles in a current database, and then visually displays the detected information of the detected liquid article.

Embodiment 2

Figure 2:
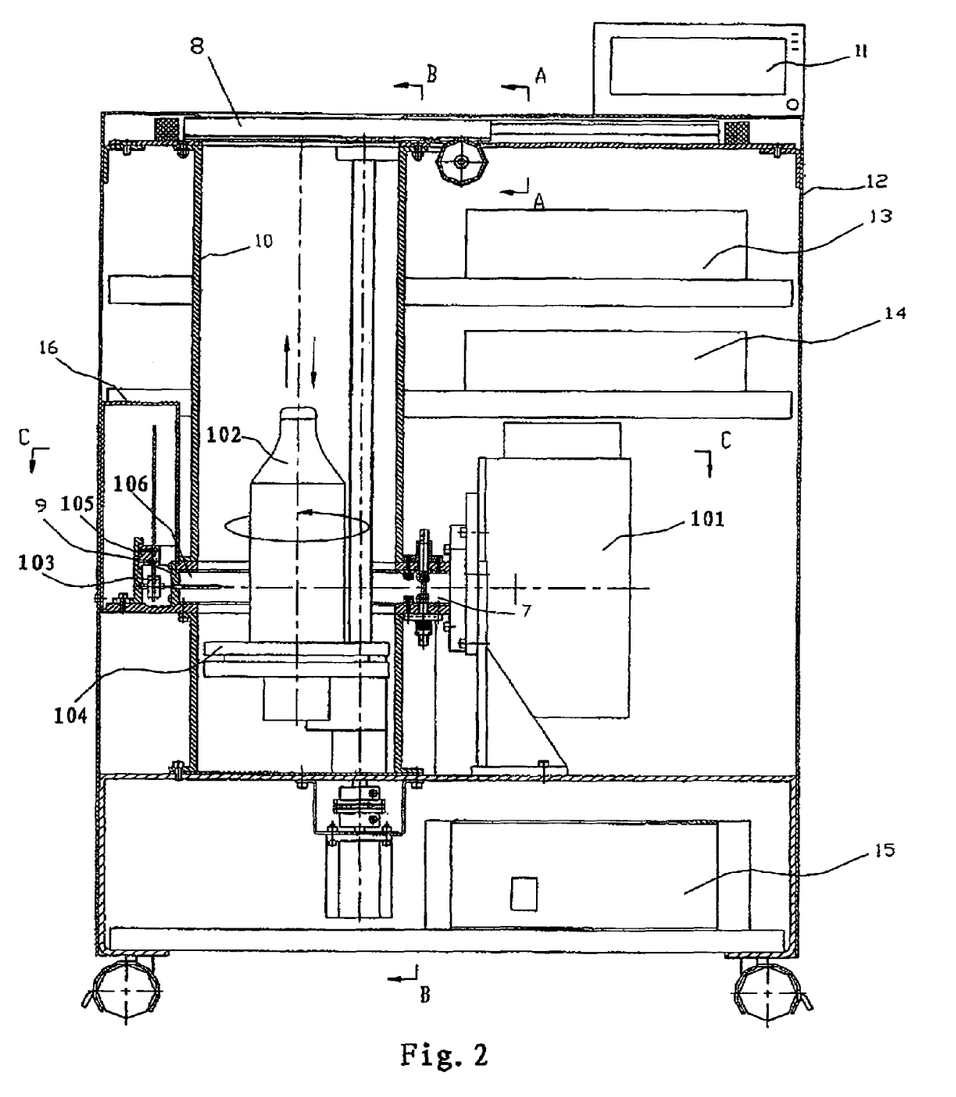
FIG. 2 is a diagram of the general structure of Embodiment 2 of the invention.

Referring to FIG. 2, the invention comprises a frame 12, a radiation source 101 employing an X-ray machine or an isotope, a detector 103 employing a solid detector or a gas detector, a beam guiding box 106, a data collecting and image processing computer 14, a system control box 13, a touch screen 11 which can display the examination result, a radiation source controller 15, and a rotary disk lifting device 104 on which a liquid article 102 to be examined can be placed. The rotary disk lifting device 104 is located in a shield cartridge 10, which is fixed on one side in the frame 12. On the upper opening end of the shield cartridge 10 and on the upper portion of the frame 12 there is provided with a protection shield door 8 which can close the shield cartridge 10. The outer wall of the shield cartridge 10 is provided with the beam guiding box 106. The front and rear ends of the beam guiding box 106 are respectively connected with a front collimator device 7 and a rear collimator 9. The front collimator device 7 is fixed with the radiation source 101. The corresponding position of the rear collimator 9 is provided with a device for adjusting horizontally the detector 105. The detector 103 is mounted to the device for adjusting horizontally the detector 105. On the other side in the frame 12 and at the bottom of the radiation source 101 there is mounted the radiation source controller 15. To the upper portion of the radiation source 101 there are successively mounted the data collecting and image processing computer 14 and the system control box 13. To the top of the frame there is mounted the touch screen 11.

Figure 3:
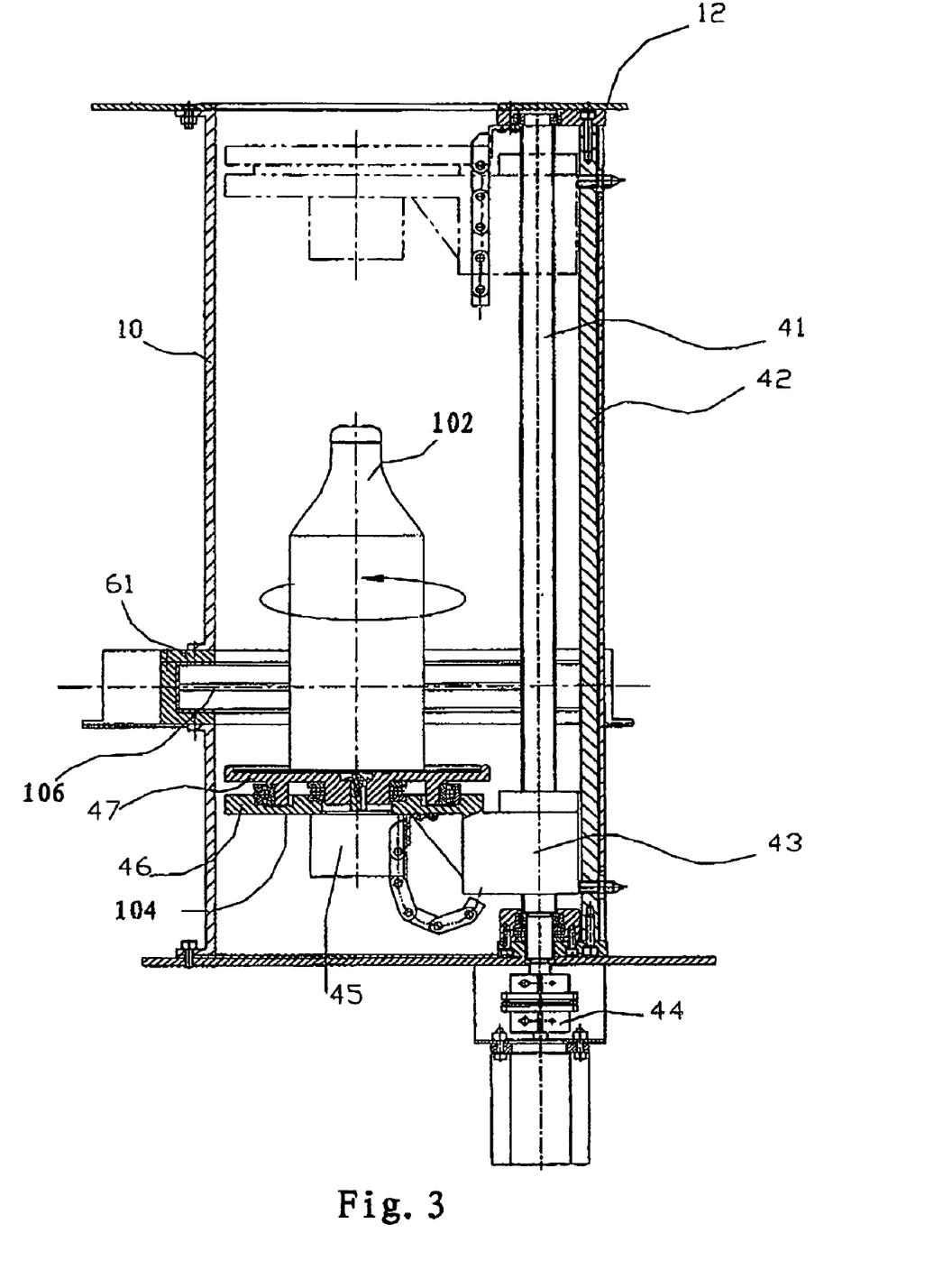
FIG. 3 is a sectional view taken along direction B-B in FIG. 2.

Referring to FIG. 2 and FIG. 3, the rotary disk lifting device 104 of the invention comprises a linear slide rail 42, a lead screw 41, a slider carrier 43, a first electric motor 44, and a rotary disk carrier 46 and a rotary disk 47 which have a second electric motor 45. The linear slide rail 42 is fixed to the inner wall of the shield cartridge 10 and embedded movably in the slider carrier 43. The slider carrier 43 is provided inside with an internal thread and thread-connected with the lead screw 41 which is fixed to the upper and lower ends inside the shield cartridge 10, and the bottom end of the lead screw 41 is connected with the first electric motor 44. The external edge of the slider carrier 43 is connected with the rotary disk carrier 46 fixed with the second electric motor 45. On the rotary disk carrier 46 there is provided with a rotary disk 47 which is connected with the output end of the second electric motor 45.

Figure 4:
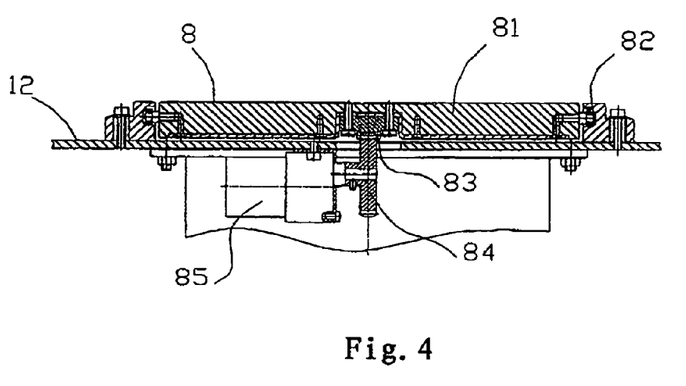
FIG. 4 is a sectional view taken along direction A-A in FIG. 2.

Referring to FIG. 2 and FIG. 4, the protection shield door 8 of the invention comprises a door plate 81, two side slide rails 82, a gear rack 83, a gear 84, and an electric motor 85. The two side slide rails 82 are fixed to the upper plane of the frame 12 and slidably connected with the door plate 81 by bearings, and at the bottom of the door plate 81 is fixed with the gear rack 83 which engages with the gear 84. The gear 84 is connected with the shaft of the electric motor 85 fixed to the lower plane of the frame 12.

Figure 5:
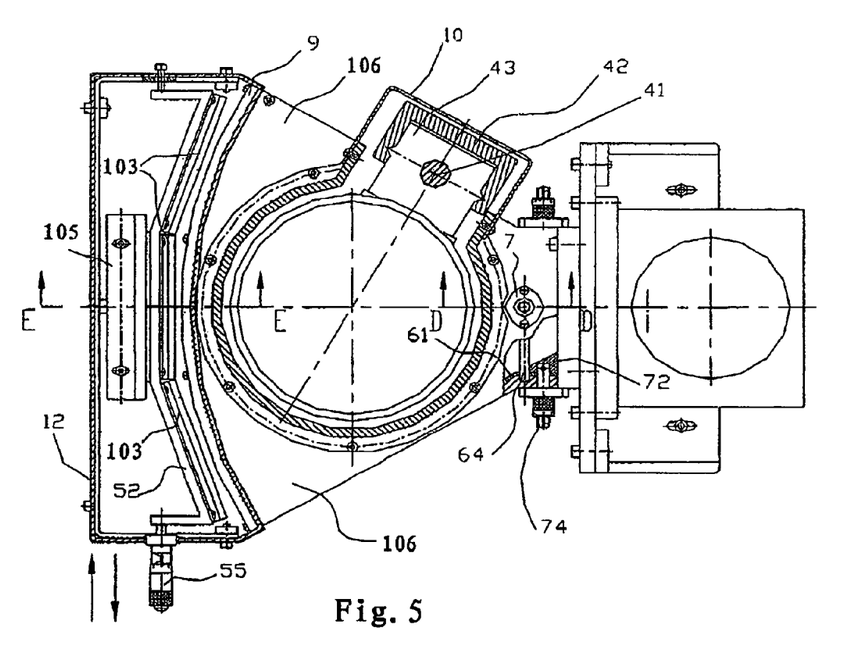
FIG. 5 is a sectional view taken along direction C-C in FIG. 2.

Referring to FIG. 2 and FIG. 5, the shape of the cross section of the beam guiding box 106 of the invention is a sector, and the inner wall of the beam guiding box 106 is provided with a protection shield layer 61.

Figure 6:
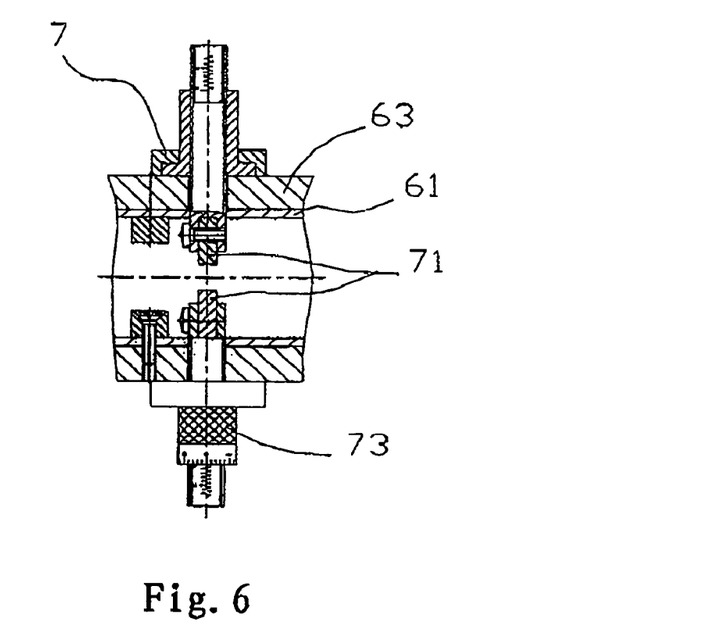
FIG. 6 is a sectional view taken along direction D-D in FIG. 5.
Figure 7:
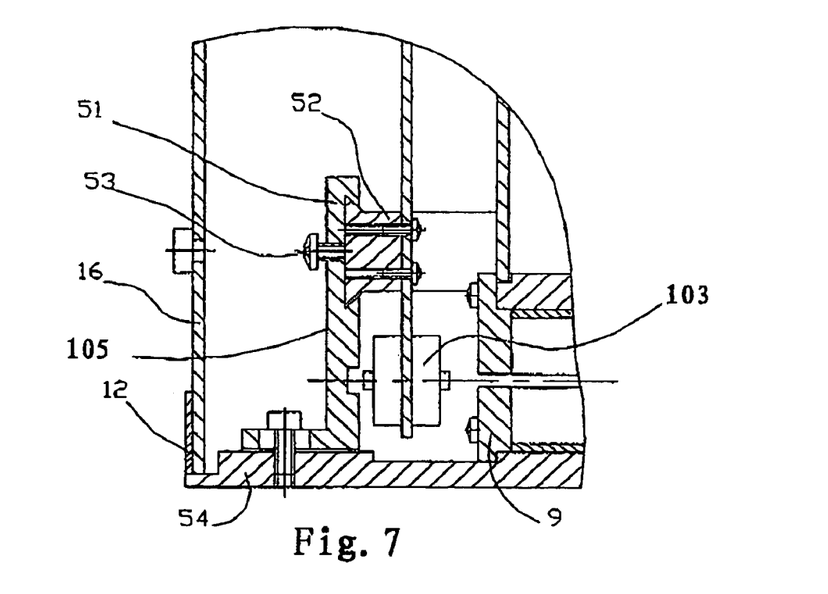
FIG. 7 is a sectional view taken along direction E-E in FIG. 5.

Referring to FIG. 5, FIG. 6 and FIG. 7, the front collimator device 7 of the invention comprises an up and down sliding stoppers 71, a left and right sliding stoppers 72, and a housing 63 connected with the beam guiding box 106. The up and down sliding stoppers 71 is embedded in a longitudinal slide slot 64 of the housing 63, and is adjusted by a indexing head first push rod 73 which is connected with the up and down sliding stoppers 71 and slidably fitted to the upper and lower wall surfaces of the housing 63, to longitudinally move. The left and right sliding stoppers 72 is embedded in a lateral slide slot of the housing 63, and is adjusted by a indexing head second push rod 74 which is connected with the left and ride sliding stopper 72 and slidably fitted to the two side wall surfaces of the housing 63, to laterally move. The rear collimator 9 is constituted by an arc form plate cut with a slit or an arc form plate with grates.

Referring to FIG. 2, FIG. 5 and FIG. 7, the detector adjusting device 105 comprises a dovetail slot holder 51 and a slide frame 52 which can embedded in the dovetail slot of the dovetail slot holder 51. The dovetail slot holder 51 is fixed on a support plate 54 which is connected with the rear collimator 9 and the frame 12. The detector 103 is mounted on the slide frame 52 and faces a beam exit of the rear collimator 9. The lateral displacement of the slide frame 52 is adjusted by a indexing head third push rod 55 which is fixed to the frame 12. On the dovetail slot holder 51 there is provided with screws 53 by which the slide frame 52 can be fixed. The periphery of the detector adjusting device 105 is provided with a detector protection case 16.

The main steps in the application of the invention are;

1) Turn on the power supplies of the radiation source 101, the data collecting and image processing computer 14, and respective electric motors of the rotary disk lifting device 104 and the protection shield door 8, which are controlled by the radiation source controller 15 and the system control box 13, and place a liquid article 102 to be detected onto the rotary disk 47 of the rotary disk lifting device 104, 2) Close the protection shield door 8, and the ray emitted from the radiation source 101 passes through the liquid article 102 and is formed into projection data by the detector 103 which faces the ray beam, and the data collecting and image processing computer 14. The system control box 13 controls the rotary disk lifting device 104 to rotate and lift the liquid article 102 at a certain speed. The detector 103 and the data collecting and image processing computer 14 sample continuously to obtain a lot of projection data of a plurality of cross sections of the liquid article 102.

Figure 8:
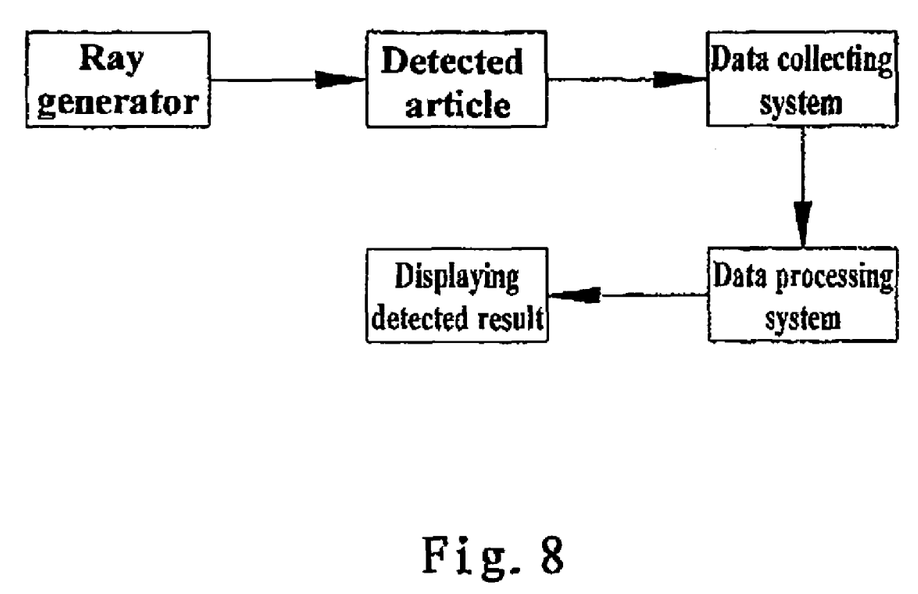
FIG. 8 is an operation principle diagram of Embodiment 2 of the invention.

3) The projection data is transmitted to the computer data processor, which corrects and reconstructs it to calculate the liquid density of the detected liquid article, compares the result with the densities of dangerous articles in a current database, and then displays the detected information of the detected liquid article 102 by means of the touch screen 11. The operation principle of the present embodiment of the invention is shown in FIG. 8.

Of course in the application steps of the invention, there further comprises that the beam width and receiving orientation may be adjusted by use of the front collimator device 7 and the detector adjusting device 105, which is not repeated here. It should be noted that according to the technical solutions of the invention, the persons skilled in the art, by use of the common-known knowledge, can make alterations to the such technical solutions, for example, changing the rotary disk lifting device 104 and the protection shield door 8 into a control of hydraulic system oil pumps and hydraulic motors; transforming the mounting positions of the radiation source controller 15, the data collecting and image processing computer 14, the system control box 13, and the touch screen 11; and etc., and thus formed technical solutions and the like should all be within the protection scope of the invention.

The invention claimed is:

1. A CT method for liquid safety-detection with a radiation source, comprising using a radiation source, a detector and data collector, and a computer data processor; and the method comprises the main steps of:
   1) placing a liquid article to be detected onto a rotary platform which is rotatable;
   2) emitting a ray from the radiation source, and passing the ray through the liquid article, and receiving the ray and forming it into projection data by the detector and data collector;
   3) transmitting the projection data to the computer data processor; processing the projection data to obtain a liquid density of the liquid article; and
   4) comparing said liquid density of the liquid article with densities of dangerous articles in a current database, and then visually displaying information of the detected liquid article.

2. A CT apparatus for liquid safety-detection with a radiation source, comprising a radiation source, a detector and data collector, and a computer data processor, said detector and data collector having integral modular structure, in the data collector a data amplifying and shaping circuit being included, in the computer data processor a database of substance densities of dangerous articles being included, wherein said radiation source is located on one side of a rotary platform mechanism on which a liquid article to be detected is placed, that said detector and data collector is located on other side of the rotary platform mechanism and faces X, γ ray beams emitted from the radiation source, and that data output cables for the detector and data collector are connected with the computer data processor.

3. The CT apparatus according to claim 1, wherein said radiation source employs an X-ray machine or an isotope source.

4. The CT apparatus according to claim 2 or 3, wherein said detector employs a solid detector or a gas detector.

5. The CT apparatus according to claim 4, wherein said data collector operates in an electric current integrating manner or in a counting manner.

6. The CT apparatus according to claim 5, wherein coordinate operations of said radiation source, the detector and collector, the computer data processor and the rotary platform mechanism are controlled synchronously by a provided scanning controller.

7. A CT apparatus for carrying out safety-examination of a liquid article by means of a radiation source, comprising a frame, a radiation source, a detector, a beam guiding box, a data collecting and image processing computer, a system control box, a radiation source controller, and a rotary disk lifting device on which a liquid article to be examined is placed, said rotary disk lifting device being located in a shield cartridge, the shield cartridge being fixed on one side in the frame, and at the upper opening end of the shield cartridge and at the upper portion of the frame there is provided with a protection shield door which closes the shield cartridge, on the outer wall of the shield cartridge there being provided with the beam guiding box, the front and rear ends of which are respectively connected with a front collimator device and a rear collimator, the front collimator device being fixedly connected with the radiation source, and the corresponding position of the rear collimator being provided with a device for adjusting horizontally the detector on which the detector is mounted; on the other side in the frame and at the bottom of the radiation source there being mounted the radiation source controller, to the upper portion of the radiation source there being successively mounted the data collecting and image processing computer and the system control box, and to the top of the frame and outside of the frame there being mounted a touch screen which displays the examination result.

8. The CT apparatus for carrying out safety-examination of a liquid article by means of a radiation source according to claim 7, wherein said rotary disk lifting device comprises a linear slide rail, a lead screw, a slider carrier, a first electric motor, a rotary disk, and a rotary disk carrier which is provided with a second electric motor, that the linear slide rail is fixed to the inner wall of the shield cartridge and embedded movably in the slider carrier, that the slider carrier is provided inside with an internal thread and thread-connected with the lead screw which is rotatably fixed at the upper and lower ends inside the shield cartridge, that the bottom end of the lead screw is connected with the first electric motor fixed to the frame, that the external edge of the slider carrier is connected with the rotary disk carrier fixed with the second electric motor, and that on the rotary disk carrier there is provided with the rotary disk which is connected with the output end of the second electric motor.

9. The CT apparatus for carrying out safety-examination of a liquid article by means of a radiation source according to claim 7, wherein said protection shield door comprises a door plate, two side slide rails, a gear rack, a gear, and an electric motor, that the two side slide rails are fixed to a upper plane of a top plate of the frame and slidably connected with the door plate by bearings, and that the gear rack fixed at the bottom of the door plate engages with the gear, which is connected with the output shaft of the electric motor fixed to the lower plane of the top plate of the frame.

10. The CT apparatus for carrying out safety-examination of a liquid article by means of a radiation source according to claim 7, 8 or 9, wherein the said beam guiding box has a cross section of the shape of a sector, and the inner wall of the beam guiding box is provided with a protection shield layer.

11. The CT apparatus for carrying out safety-examination of a liquid article by means of a radiation source according to claim 10, wherein said front collimator device comprises an up and down sliding stoppers, a left and right sliding stoppers, and a housing connected with the beam guiding box, that the up and down sliding stoppers are embedded in a longitudinal slide slot of the housing and are adjusted by a indexing head first push rod which is connected with the up and down sliding stoppers and slidably fitted to the upper and lower wall surfaces of the housing, to longitudinally move, and that the left and right sliding stoppers are embedded in a lateral slide slot of the housing and are adjusted by a indexing head second push rod which is connected with the left and ride sliding stopper and slidably fitted to the two side wall surfaces of the housing, to laterally move.

12. The CT apparatus for carrying out safety-examination of a liquid article by means of a radiation source according to claim 10, wherein said rear collimator is constituted by an arc form plate cut with a slit or an arc form plate with grates.

13. The CT apparatus for carrying out safety-examination of a liquid article by means of a radiation source according to claim 12, wherein said detector adjusting device comprises a dovetail slot holder and a slide frame which can embedded in the dovetail slot of the dovetail slot holder, that the dovetail slot holder is fixed on a support plate which is connected with the rear collimator and the frame, that the detector is mounted on the slide frame, faces a beam exit of the rear collimator, and is laterally displaced by means of the adjustment of the slide frame by a indexing head third push rod which is fitted to the frame, and that on the dovetail slot holder there is provided with screws by which the slide frame is fixed.

14. The CT apparatus for carrying out safety-examination of a liquid article by means of a radiation source according to claim 13, wherein on the periphery of said detector adjusting device there is provided with a detector protection case.

15. The CT apparatus for carrying out safety-examination of a liquid article by means of a radiation source according to claim 14, wherein said radiation source is an X-ray machine or an isotope source, and that the detector is a solid or gas detector.

16. The CT apparatus for carrying out safety-examination of a liquid article by means of a radiation source according to claim 7, wherein on external side the top of the frame there is mounted a touch screen which displays the examination result.

* * * * *

UNITED STATES PATENT AND TRADEMARK OFFICE
CERTIFICATE OF CORRECTION

PATENT NO.         : 7,508,908 B2
APPLICATION NO. : 11/286559
DATED              : March 24, 2009
INVENTOR(S)        : Haifeng Hu et al.

It is certified that error appears in the above-identified patent and that said Letters Patent is hereby corrected as shown below:

Title page
Item (73) Assignees:    delete "Nuntech Company Limited" and insert
--Nuctech Company Limited--.

Signed and Sealed this

Eighteenth Day of August, 2009

David J. Kappos
*Director of the United States Patent and Trademark Office*